United States Patent
Boyd et al.

(10) Patent No.: US 8,251,731 B2
(45) Date of Patent: Aug. 28, 2012

(54) ELECTRICAL CONNECTION SYSTEM AND METHOD FOR IMPLANTABLE MEDICAL DEVICES

(75) Inventors: Garth W. Boyd, Ellington, CT (US); Michael Poppy, New Richmond, WI (US); Michael Grant, Cambridge, MN (US)

(73) Assignee: Deringer-Ney, Inc., Bloomfield, CT (US)

( * ) Notice: Subject to any disclaimer, the term of this patent is extended or adjusted under 35 U.S.C. 154(b) by 121 days.

(21) Appl. No.: 12/882,460

(22) Filed: Sep. 15, 2010

(65) Prior Publication Data

US 2011/0065301 A1    Mar. 17, 2011

Related U.S. Application Data (60) Provisional application No. 61/242,458, filed on Sep. 15, 2009.

(51) Int. Cl.
*H01R 4/50* (2006.01)
(52) U.S. Cl. .................. 439/347; 439/281; 439/359
(58) Field of Classification Search ............ 439/347, 439/281, 160, 378, 359, 152, 155, 923, 909
See application file for complete search history.

(56) References Cited

U.S. PATENT DOCUMENTS

| | | | |
|---|---|---|---|
| 3,001,170 A | 9/1961 | Eyre et al. | |
| 3,187,295 A | 6/1965 | Husaka | |
| 3,215,973 A | 11/1965 | Falconer | |
| 3,848,951 A | 11/1974 | Michaels et al. | |
| 4,070,086 A | 1/1978 | Trafford | |
| 4,077,697 A | 3/1978 | Yates | |
| 4,401,958 A | 8/1983 | Noorigian | |
| 4,537,457 A | 8/1985 | Davis, Jr. et al. | |
| 5,022,404 A | 6/1991 | Hafner | |
| 5,222,164 A | 6/1993 | Bass et al. | |
| 5,380,214 A | 1/1995 | Ortega, Jr. | |
| 5,413,595 A * | 5/1995 | Stutz, Jr. ..................... | 607/37 |
| 5,460,549 A * | 10/1995 | Muzslay ................ | 439/733.1 |
| 5,645,577 A | 7/1997 | Froberg et al. | |

(Continued)

FOREIGN PATENT DOCUMENTS

EP      1 737 078 A1      12/2006

(Continued)

OTHER PUBLICATIONS http://www.integra-ls.com/products/?product=55, website, first published Aug. 16, 2004.

(Continued)

*Primary Examiner* — Phuong Dinh
(74) *Attorney, Agent, or Firm* — Dorsey & Whitney LLP

(57) ABSTRACT

A multiple contact connector interfaces between an implanted medical device and an implanted cable or lead. A connector connects between multiple implanted leads, each of which has multiple independent conductors. The connection system is a planar array of male connector pins on one portion, and a matching array of female connector receptacles on a second portion. Alignment via alignment features and pressing together the portions allows pins to engage with the receptacles providing a secure electrical connection. Sealing features on the connector apparatus seal out external fluids and isolate fluid present in the connector apparatus prior to mating, which electrically isolates each pin and its corresponding receptacle from other pin and receptacle pairs. Latching features retains the relative position of the pins, receptacle, and the positioning of the fluid seals, and is reversible for removal of the connector.

13 Claims, 9 Drawing Sheets

U.S. PATENT DOCUMENTS

| | | | |
|---|---|---|---|
| 5,690,509 | A | 11/1997 | Eisenbraun |
| 5,704,802 | A | 1/1998 | Loudermilk |
| 5,748,821 | A * | 5/1998 | Schempp et al. ............... 385/76 |
| 5,755,743 | A | 5/1998 | Volz et al. |
| 5,843,141 | A | 12/1998 | Bischoff et al. |
| 5,951,595 | A | 9/1999 | Moberg et al. |
| 6,016,447 | A | 1/2000 | Juran et al. |
| 6,016,448 | A | 1/2000 | Busacker et al. |
| 6,029,089 | A | 2/2000 | Hawkins et al. |
| 6,080,188 | A | 6/2000 | Rowley et al. |
| 6,112,121 | A | 8/2000 | Paul et al. |
| 6,154,675 | A | 11/2000 | Juran et al. |
| 6,293,596 | B1 | 9/2001 | Kinder |
| 6,312,297 | B1 | 11/2001 | Lorkowski |
| 6,321,126 | B1 | 11/2001 | Kuzma |
| 6,390,843 | B1 | 5/2002 | Lim |
| 6,409,530 | B1 | 6/2002 | Zhao et al. |
| 6,428,368 | B1 | 8/2002 | Hawkins et al. |
| 6,551,142 | B2 | 4/2003 | Eisenbraun |
| 6,721,600 | B2 | 4/2004 | Jorgenson et al. |
| 6,878,013 | B1 | 4/2005 | Behan |
| 6,929,517 | B2 | 8/2005 | Tsai |
| 6,963,780 | B2 | 11/2005 | Ruben et al. |
| 6,971,907 | B1 | 12/2005 | Stroud |
| 7,012,542 | B2 | 3/2006 | Powell et al. |
| 7,047,083 | B2 | 5/2006 | Gunderson et al. |
| 7,070,455 | B2 | 7/2006 | Balsells |
| 7,087,077 | B1 | 8/2006 | Van Dijk et al. |
| 7,128,757 | B2 | 10/2006 | Boylan et al. |
| 7,187,975 | B2 | 3/2007 | Flickinger et al. |
| 7,195,523 | B2 | 3/2007 | Naviaux |
| 7,244,150 | B1 | 7/2007 | Brase et al. |
| 7,286,882 | B2 | 10/2007 | Cole |
| 7,347,751 | B2 | 3/2008 | Sweeney et al. |
| 7,510,447 | B2 | 3/2009 | Drew |
| 7,526,339 | B2 | 4/2009 | Lahti et al. |
| 7,534,127 | B2 | 5/2009 | Parker et al. |
| 7,798,864 | B2 | 9/2010 | Barker et al. |
| 7,819,682 | B2 | 10/2010 | Donetsky |
| 2001/0053631 | A1 | 12/2001 | Nagai |
| 2002/0002016 | A1 | 1/2002 | Sato et al. |
| 2003/0003796 | A1 * | 1/2003 | Zoiss ........................... 439/455 |
| 2004/0106964 | A1 | 6/2004 | Fischer, Sr. et al. |
| 2004/0153138 | A1 | 8/2004 | Murphy |
| 2004/0162593 | A1 | 8/2004 | Jorgenson et al. |
| 2005/0186829 | A1 | 8/2005 | Balsells |
| 2007/0161294 | A1 | 7/2007 | Brase et al. |
| 2007/0179553 | A1 | 8/2007 | Iyer et al. |
| 2007/0225772 | A1 | 9/2007 | Lahti et al. |
| 2007/0280850 | A1 | 12/2007 | Carlson |
| 2008/0195194 | A1 | 8/2008 | Pacetti et al. |
| 2008/0274651 | A1 | 11/2008 | Boyd et al. |
| 2009/0208168 | A1 * | 8/2009 | Ishikawa et al. ................ 385/14 |
| 2011/0022100 | A1 | 1/2011 | Brase et al. |
| 2011/0151698 | A1 | 6/2011 | Boyd et al. |

FOREIGN PATENT DOCUMENTS

| | | |
|---|---|---|
| GB | 2227612 | 8/1990 |
| WO | WO 02/095877 A1 | 11/2002 |
| WO | WO 2007/070544 | 6/2007 |

OTHER PUBLICATIONS

Harris et al., "A study of some palladium-tin, silver-tin and palladium-silver-tin alloys," *Journal of the Less-Common Metals*, Elsevier-Sequoia, S.A. Lausanne, CH, 16(3): 223-232 (Nov. 1, 1968).

Schenck, J.F., "The Role of Magnetic Susceptibility in Magnetic Resonance Imaging: MRI Magnetic Compatibility of the First and Second Kinds," Medical Physics, AIP, Melville, NY, vol. 23, No. 6 (Jun. 1, 1996).

* cited by examiner

ELECTRICAL CONNECTION SYSTEM AND METHOD FOR IMPLANTABLE MEDICAL DEVICES

CROSS-REFERENCE TO RELATED APPLICATIONS

This application claims priority to U.S. Application No. 61/242,458, entitled Electrical Connection System and Method for Implantable Medical Device," filed Sep. 15, 2009, the content of which is incorporated herein by reference in its entirety.

FIELD OF THE INVENTION

The present invention pertains to electrical connection systems, or assemblies, and methods, and more particularly to assemblies and methods facilitating electrical connections of medical electrical conductors to medical devices.

BACKGROUND

Many medical devices include electrical connection assemblies for coupling with a medical electrical lead connector that is formed along the proximal portion of the lead and includes a plurality of connector elements disposed along a length thereof.

These assemblies typically include a plurality of electrical contacts positioned within an area, or bore, of what is typically called a connector module, or header, at locations corresponding to the connector elements of the lead connector, in order to mate with the corresponding connector elements when the connector is inserted within the bore. Some device connection assemblies further include sealing elements located between the electrical contacts to mate with insulating zones located between the connector elements of the lead connector, and thereby provide electrical isolation between each mating contact and connector element. Although a variety of connector assembly configurations are known in the art, there is still a need for new methods and assembly designs that provide stable electrical connections, and isolation between the connections, without substantially increasing the size or volume of the implanted system, and without adding time nor significant effort to surgical procedure to secure the connections.

In addition the number of connector elements is increasing as novel therapies require higher numbers of electrodes on the distal end of the lead. Historically, the plurality of connections is secured with a dedicated set screw for each connection. The set screws providing positional stability to the relative position of the lead and connector block, as well as providing the necessary forces to electrically mate the pairs of connections. As the number of contacts in implantable systems continue to increase, it becomes unreasonable to use the traditional methods and apparatus. There are limitations both to the physical size of the connector systems, and also to the magnitude of manual manipulation required during a surgical procedure.

SUMMARY

A multiple contact connector interfaces between an implanted medical device and an implanted cable or lead to provide an electrical connection for implanted medical applications, including implanted therapeutic and sensing applications. According to one embodiment, a connector system for establishing an electrical connection between an implanted medical device and a lead includes an array of electrically active pins and complementary electrically conductive receptacles, in which one of the array and the complementary receptacles are provided in a recessed area of the implanted medical device and are exposed from the implanted medical device prior to establishing the electrical connection, and the other of the array and the complementary receptacles are encased in a lead housing from which a distal end of the lead extends. The electrical connection is established upon pressing the pins and the complementary receptacles together, and upon establishing the electrical connection, the lead housing is exposed at an exterior of the implanted medical device.

According to another embodiment, a connector system for establishing an electrical connection between an implanted medical device and a lead includes: a connector with a body portion that houses a plurality of electrically active contacts and a flange portion extending from the body portion, where the lead extends from the connector and is coupled to the electrically active contacts; an implanted medical device with a plurality of electrically conductive contacts in a recessed area of the implanted medical device that are exposed from an exterior of the implanted medical device prior to establishing the electrical connection; and a seal. The electrically active contacts and the electrically conductive contacts establish the electrical connection upon inserting the body portion into the recessed area, and upon establishing the electrical connection, the seal is arranged between the connector and the implanted medical device and protects the electrical connection from fluids.

In yet another embodiment, a connector system for establishing an electrical connection between an implanted medical device and a lead includes a first and a second connector block, the first and the second connector blocks each having a body portion that houses a plurality of electrically active contacts, a flange portion extending from the body portion, and a lead extending from the connector block, and an implanted medical device comprising a plurality of electrically conductive contacts arranged in each of a first and a second recessed area of the implanted medical device, where the electrically conductive contacts are exposed from an exterior of the implanted medical device prior to establishing the electrical connection. The body portion of the first and the second connector blocks are differently shaped from one another, and the first and the second recessed areas include sidewalls complementary to respective shapes of the first body portion and the second body portion, such that the electrical connection may only be established between the first connector block and the first recessed area and the second connector block and the second recessed area.

Additionally, embodiments provide a connector for connecting between multiple implanted leads, each of which has multiple independent conductors.

Electrical connection systems include planar arrays of male connector pins on one portion of the apparatus, and matching arrays of female connector receptacles on a second portion of the apparatus. The two portions of the connector are joined by aligning the arrays of pins and receptacles and pressing together the portions such that the pins are engaged with the receptacles and a secure electrical connection is made. Alignment features in both portions of the apparatus ensure that the pins and receptacles are aligned. The connector apparatus may include features to seal out external fluids, and also to isolate any fluid existing in the connector apparatus prior to mating, so that each pin and its corresponding receptacle are electrically isolated from other pin and receptacle pairs. The apparatus may additionally or alternatively include a latching feature that retains the relative position of the pins, receptacle, and the positioning of the fluid seals. Such a latching feature may be reversible, so that the lead can be removed from the device without damage to either portion of the connector apparatus.

Electrical connection systems may provide for connection of multiple conductors, but one conductor may also be connected to using the connector apparatus disclosed. For example, certain embodiments may provide a connection for medical applications requiring 2 to 128 independent conductors. Despite the high number of connections made, the profile of the connector is relatively low because, for example, certain embodiments provide alignment and keying structures for the proper registration of the male and female portions of the connection. Additionally, each lead's connector may be uniquely keyed to ensure that only complementary connections can be made, e.g., during a surgical procedure, thus reducing the opportunity for connection related errors.

These and other features and advantages of the present invention will become apparent to those skilled in the art from the following detailed description, wherein it is shown and described illustrative embodiments of the invention, including best modes contemplated for carrying out the invention. As it will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The following description is exemplary in nature and is not intended to limit the scope, applicability, or configuration of the invention. Rather, the following description provides practical illustrations for implementing exemplary embodiments of the invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
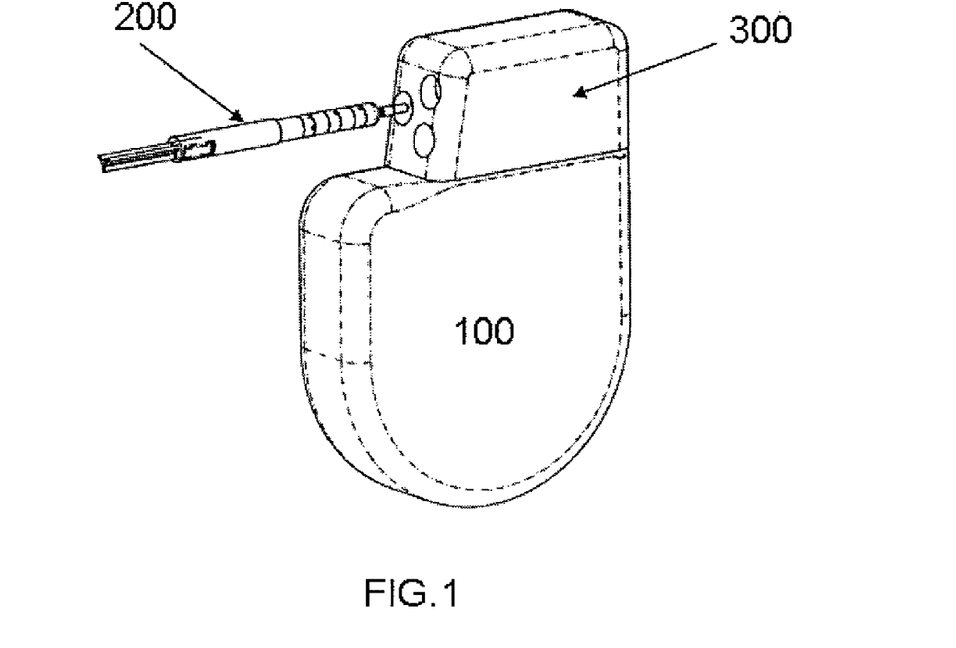
FIG. 1 is a perspective view of an implanted medical device system.

FIG. 1 is a perspective view of an implanted medical device system. The system is composed of a hermetically sealed electronics and battery compartment often referred to as the implantable pulse generator (IPG) 100, and a lead 200 composed of multiple independent conductors insulated from each other and from the body by a polymer encapsulation. The lead 200 is configured as a tubular cable that connects multiple contacts in the IPG 100 to target tissues in the body. The proximal end of the lead 200 is shown being inserted into a connector block 300, which is an integral part of the IPG 100.

Electrical connection systems according to embodiments provided herein, include planar arrays of male connector pins on one portion of the apparatus, and matching arrays of female connector receptacles on a second portion of the apparatus. The two portions of the connector are joined by aligning the arrays of pins and receptacles and pressing together the portions such that the pins are engaged with the receptacles and a secure electrical connection is made between a medical device and a lead. Traditional connector conductive surfaces are expressed as end pins or rings around a cylindrical lead body, e.g., lead 200. While leads may have various outer diameters, the conductors are arranged along a single dimension, that being the axis of the lead. In the embodiments described below, the conductors are deployed in two dimensions providing a planar surface upon which to place a larger number contacts. This planar approach eliminates the need to geometrically convert from the surface of the IPG to a cylinder, thus simplifying the structure of the IPG.

Figure 2:
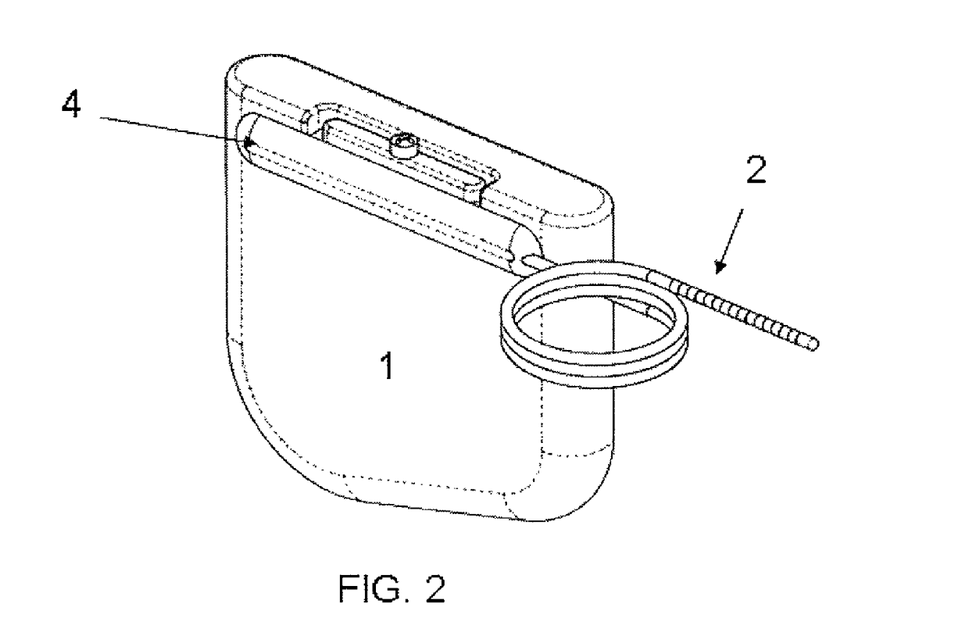
FIG. 2 is a perspective view of the implanted medical device system provided according to certain embodiments.

Accordingly, FIG. 2 is a perspective view of an implanted medical device system provided according to embodiments that implements a connector system for establishing an electrical connection between an implanted medical device and a lead, which replaces the typical connector block 300 depicted in FIG. 1. FIG. 2 depicts an implanted medical device or implanted pulse generator (IPG) 1 and the proximal portion of a lead 2 provided as a lead connector 4, e.g., the lead 2 extends from and is electrically coupled to the lead connector 4. The lead connector 4 locates in a recessed area 6 or receptacle of the IPG 1 to establish an electrical connection on the side of the IPG 1. Alternatively, the lead connector 4 may be provided on and electrically connected to the top upper end (see e.g., FIG. 8) or edge of the IPG 1, in which case the recessed area 6 is arranged in an upper wall or edge of the IPG 1. In order to establish the electrical connection, the lead connector 4 and the IPG 1 are pressed together, which results in an array of electrically active pins and complementary electrically conductive receptacles, one of which is disposed in the IPG 1, and the other of which is disposed in the lead connector 4, to contact each other. As depicted in FIG. 2, upon establishing the electrical connection, the lead housing is laterally attached to the IPG 1 and is exposed at an exterior of the implanted medical device. This is in contrast to the use of the typical connector block 300 in which the distal end of the lead 200 is inserted by sliding the lead 200 through a narrow bore extending through the connector block 300.

Figure 3:
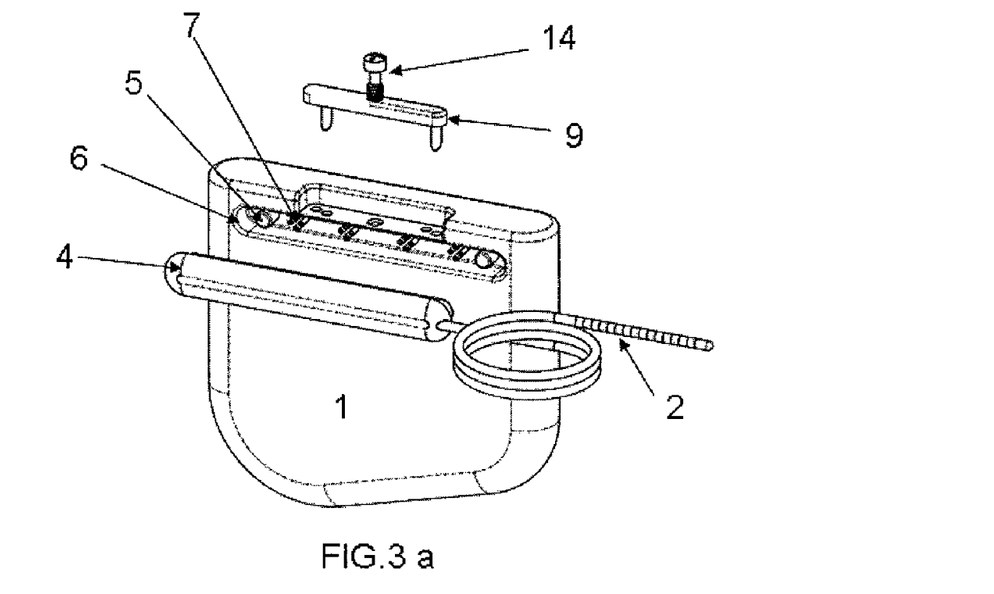
FIG. 3a is another perspective view of an embodiment that is side mounted and connects to a plurality of feed throughs with multiple pins.
FIG. 3b is a perspective view of an embodiment depicting detail of the proximal end connector of the patient lead.
FIG. 3c is an alternative perspective view of an embodiment of the connector and receptacle of an implantable pulse generator (IPG) in a non-engaged position.
FIG. 3d provides magnified, top perspective views of the connector and IPG depicted in FIG. 3c.

FIG. 3a is a perspective view of another embodiment, in which the lead connector 4 is side mounted, e.g., laterally attached, to the IPG 1 and connects to a plurality of electrical conductors with multiple pins arranged in a recessed area 6, e.g., a pocket or receptacle, provided in the IPG 1. The recessed area 6 is defined by a sidewall of the IPG 1 and is shaped to accept the lead connector 4 on the proximal end of the lead 2, .e.g., the recessed area 6 is complementarily shaped relative to lead connector 4, and thus may include a planar surface to complement a planar surface of the lead connector 4. The recessed area 6 contains multiple electrical conductors with several pins 7 each, which are exposed from the IPG 1 by way of the opened recessed area 6 prior to establishing the electrical connection. These pins 7 carry electrical power and/or signals in and out of the hermetically sealed IPG 1, e.g., to the sealed IPG can. The recessed area 6 also contains alignment structures 5, which are depicted as round posts. The structures 5 may be of various shapes to ensure alignment with the proper lead connector 4 is provided during surgical connection of the IPG 1, so that the proper lead 2 connects to the proper recessed area 6 such as in cases where there is more than one recessed area 6, and/or to provide a connection with a proper orientation of the lead connector 4 relative to the recessed area 6.

Figure 3B:
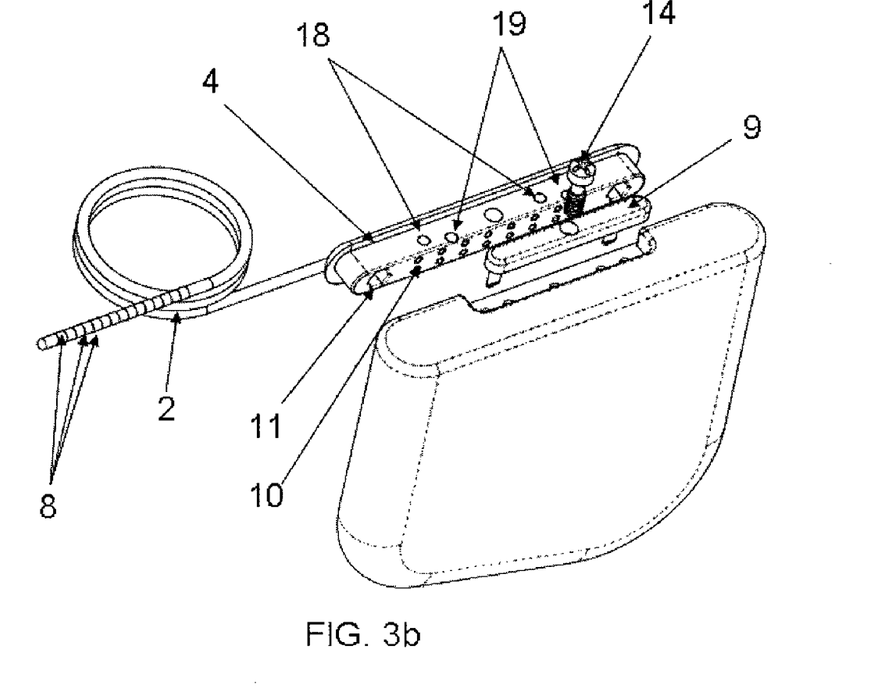

FIG. 3b is a perspective view of an embodiment depicting detail of the proximal end lead connector 4 of the patient lead 2. The distal end of the lead 2 bears the tissue contacting electrodes 8 for providing therapeutic or sensing functions, and the opposite proximal end of the lead 2 extends from the lead connector 4 housing. Embodiments of the lead connector 4 incorporate female or male structures to register and mate with the pins 7 and structures 5 depicted in FIG. 3a, and are encased in the lead connector 4, e.g., within a housing portion of the lead connector 4 having a planar surface or surface complementary to a facing surface of the recessed area 6. The electrical connector barrels or connection receptacles 10 slide over the pins 7 providing an electrical connection for each pin. The alignment structures 11 of the lead connector 4 and the alignment structures 5 (FIG. 3a) of the IPG 1 are complementarily shaped and provide for an alignment mechanism between the two portions forming the connection so that just prior to establishing the electrical connection, the aligned alignment structures correctly position the pins 7 and the connection receptacles 10.

In FIG. 3b, the surfaces of the body of the lead connector 4 are depicted. The front surface shows hexagonal alignment structures 11, as an example of an alternative configuration, and an array of connection receptacles 10, to receive electrical conductor pins 7. In FIG. 3b, the array of connection receptacles 10 contains 2 rows of 8 barrels, and is configured for connecting with an IPG recessed area 6 having a complementary array of 2 rows of 8 pins as shown in FIG. 3c.

Figure 3C:
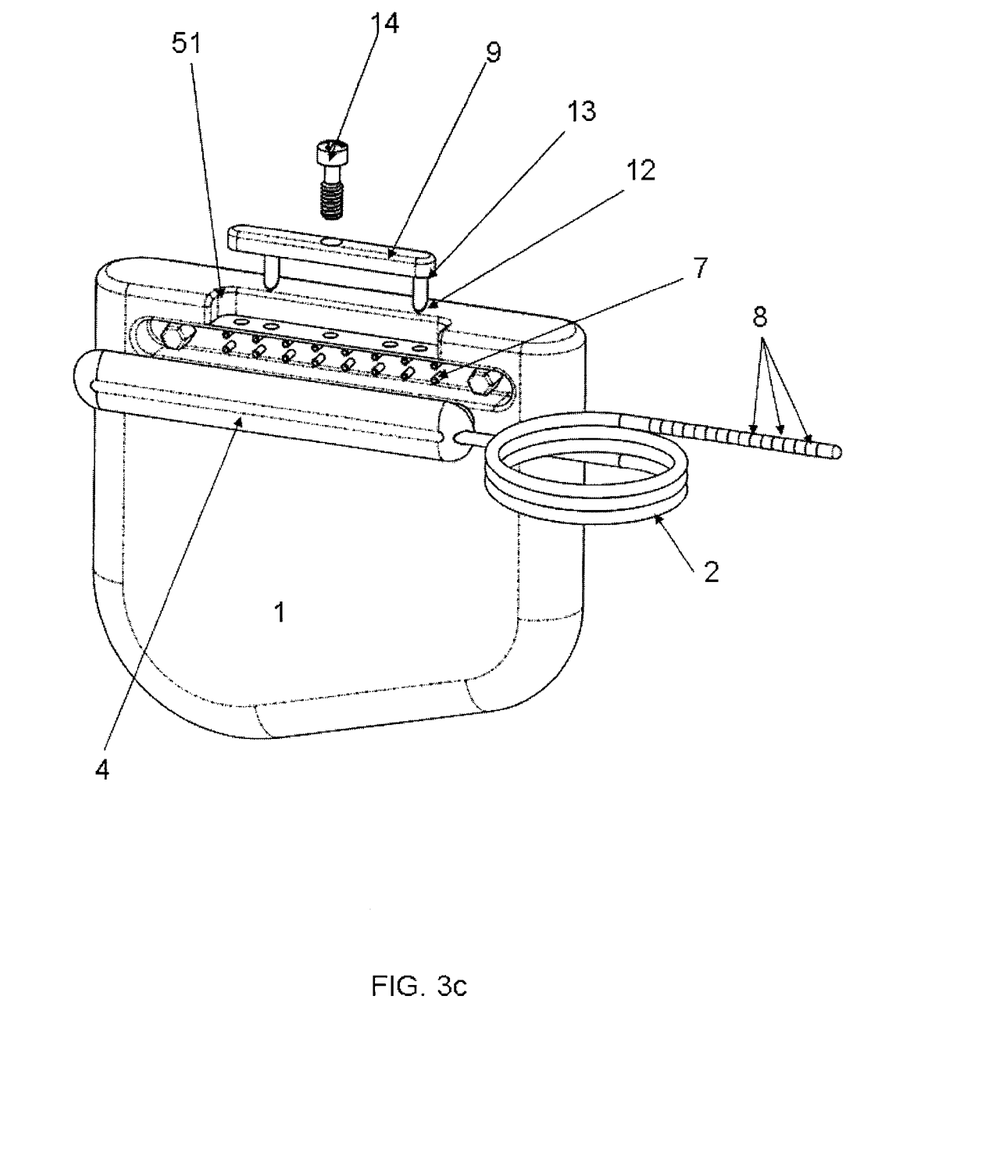

FIG. 3c is an alternative perspective view of the embodiment depicted in FIG. 3b in which the lead connector 4 and recessed area 6 of IPG 1 are in a non-engaged position. As shown in FIG. 3c, the recessed area 6 contains alignment structures 5, which are hexagonal, but may have a variety of shapes, and multiple electrical conductor pins 7. The patient lead 2 includes tissue contacting electrodes 8 on a distal end, and the lead connector 4 on the terminal or proximal end.

Figure 3D:
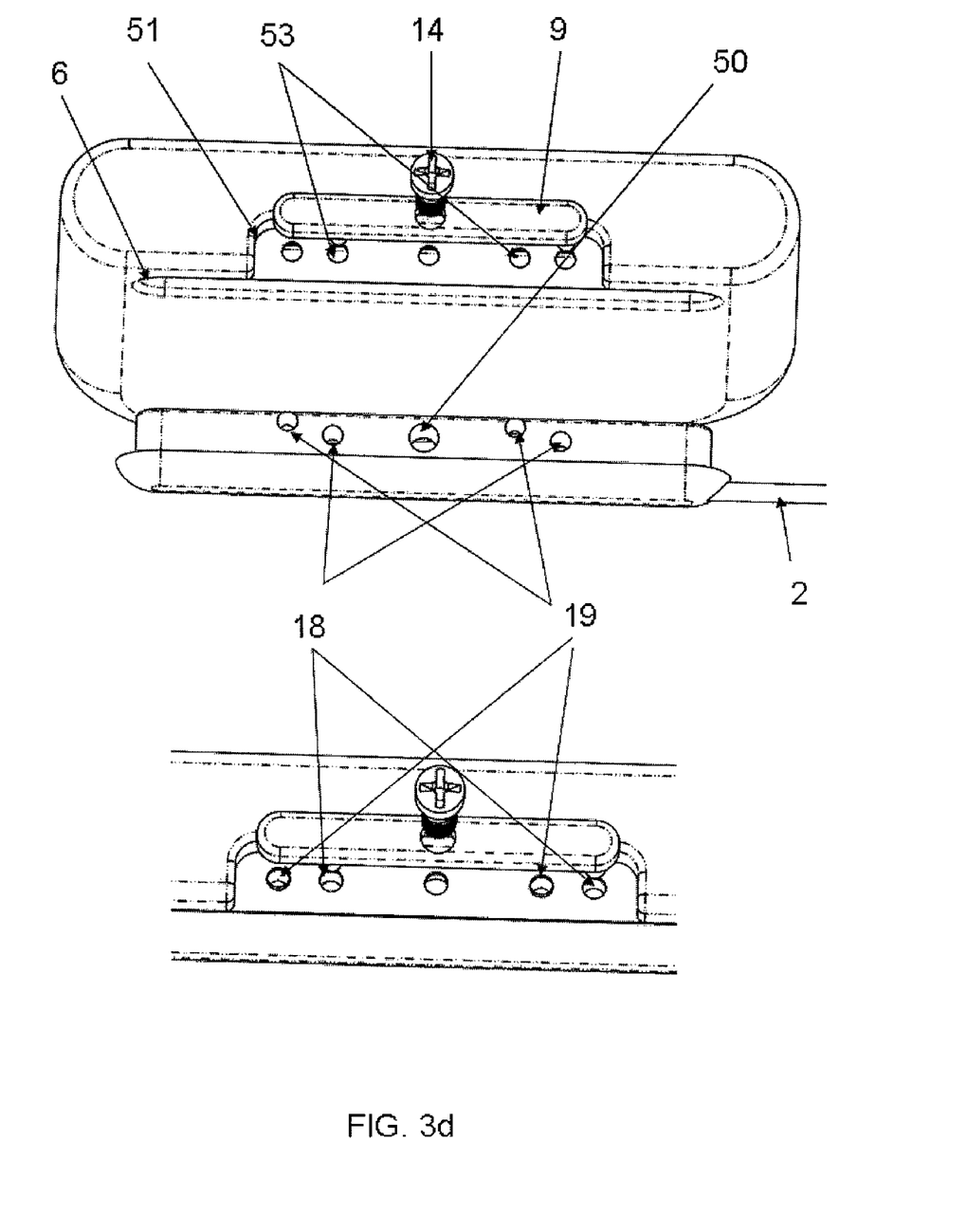

FIG. 3d depicts magnified, top perspective views of the lead connector 4 and IPG 1 during an engagement operation between the lead connector 4 and IPG 1. In the upper portion of FIG. 3d, the lead connector 4 is not yet seated into the recessed area 6 of the IPG 1. A wall 51 of the housing of the IPG 1 of metallic or other material sufficient to bear the alignment forces is shown with a number of cut-outs forming openings or apertures. Viewed from the side, the lead connector 4 includes central threaded hole 50, into which screw 14, will be turned, as well as two pairs of openings 18 and 19, which are offset from each other and asymmetric relative to the center hole 50.

To connect the lead 2 to the IPG 1, lead connector 4, is manually pressed partially into the recessed area 6. Latching device 9, is then pressed into place on the IPG 1, such that its legs 13, pass through latch openings 53 in the body of IPG 1, e.g., the latch openings 53 are formed in a wall defining the recessed area 6 so that the latch openings 53 extend into the recessed area 6, and then partly into the latch openings 18 of the lead connector 4 arranged within the recessed area 6 in order to latch the lead connector 4 to the IPG 1. If the lead connector 4 is not fully seated into the recessed area 6, the latch openings 18 will be misaligned with the IPG latch openings 53. Forcing the latch 9 downward manually or with the help of optional screw 14, will cause the chamfer 12 at the end of the latch's legs 13 to force the connecting holes 18 (FIG. 3b) into alignment and thereby draw the lead connector 4 into the recessed area 6 in a latched position of the lead connector 4, e.g., the lead connector 4 is inserted into the recessed area 6 to its fullest extent.

The bottom part of FIG. 3d shows the lead connector 4 fully seated in the recessed area 6 of the IPG 1 in the latched position. Note that connecting openings 18 are aligned, but that ejection openings 19 are misaligned.

To disconnect the lead connector 4, i.e., to eject the lead connector 4 from its latched position without damage, latch device 9 is removed from lead connector 4 and IPG 1, turned 180 degrees, e.g., reversed, and then reinserted. Upon reinsertion, the latch device 9 is inserted into openings 53, but latch device 9 legs 13 (FIG. 3c) are reversed from their original position and are aligned with ejection openings 19, rather than the connecting openings 18, due to the placement of legs 13 (FIG. 3c) on latch device 9. In particular, legs 13 (FIG. 3c) are spaced at different distances relative to the ends of latch device 9 so that rotating latch device 9 by 180 degrees results in the legs 13 (FIG. 3c) aligning with different openings 53 and with ejection openings 19, even though the planar top portion of device 9 aligns with the same area of the IPG 1. Forcing the latch device 9 downward manually, or with the help of optional screw 14, will engage the chamfer 12, now reversed, into the misaligned ejection openings 19, and via the chamfer 12, will cause ejection openings 19 to align with openings 53, thereby forcing the lead housing out of the latched position and unseating the lead connector 4 from the recessed area 6.

Figure 4:
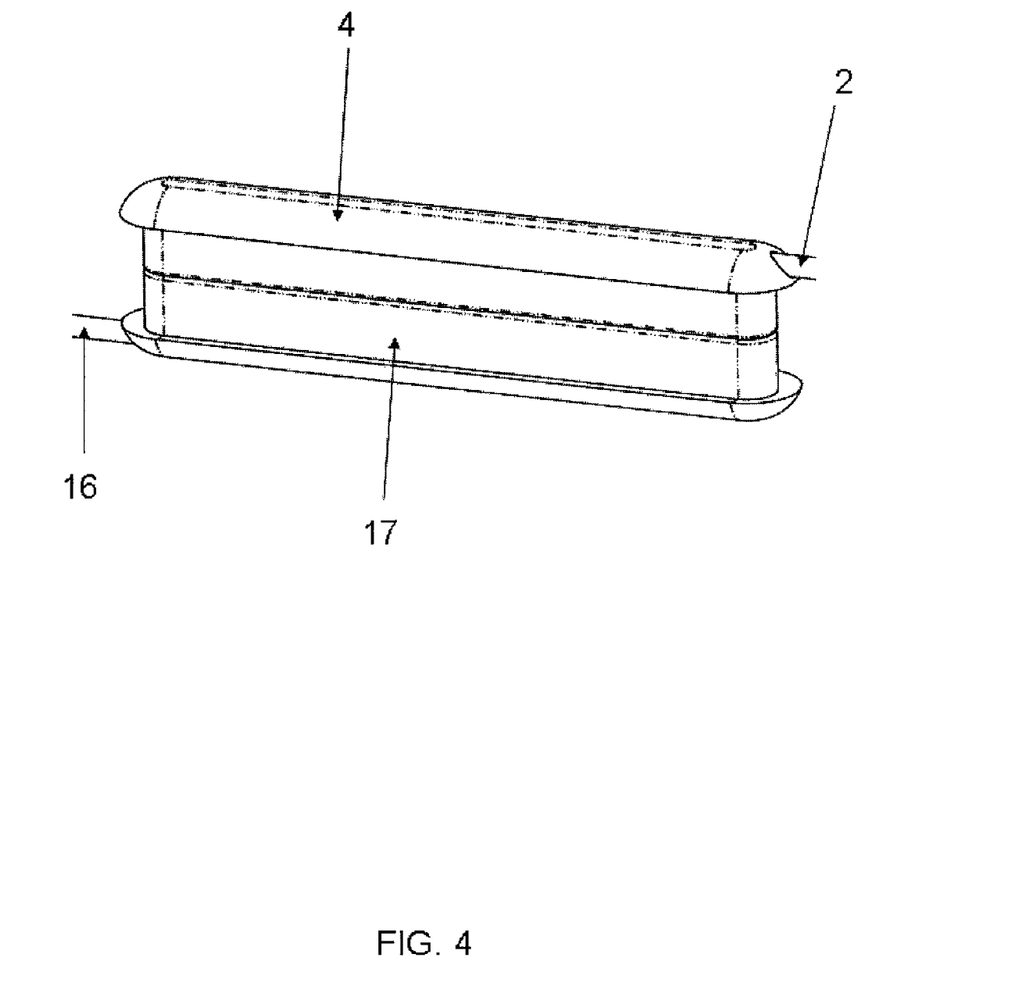
FIG. 4 provides a multi-connection connector block coupled to a companion connector, in accordance with certain embodiments.

FIG. 4 provides an embodiment of the multi-connection lead connector 4 coupled to lead 2 and a companion connector 17 on the proximal end of a lead, lead-to-adapter or extender 16, which are mated with companion male/female connectors 4 and 17.

Figure 5:
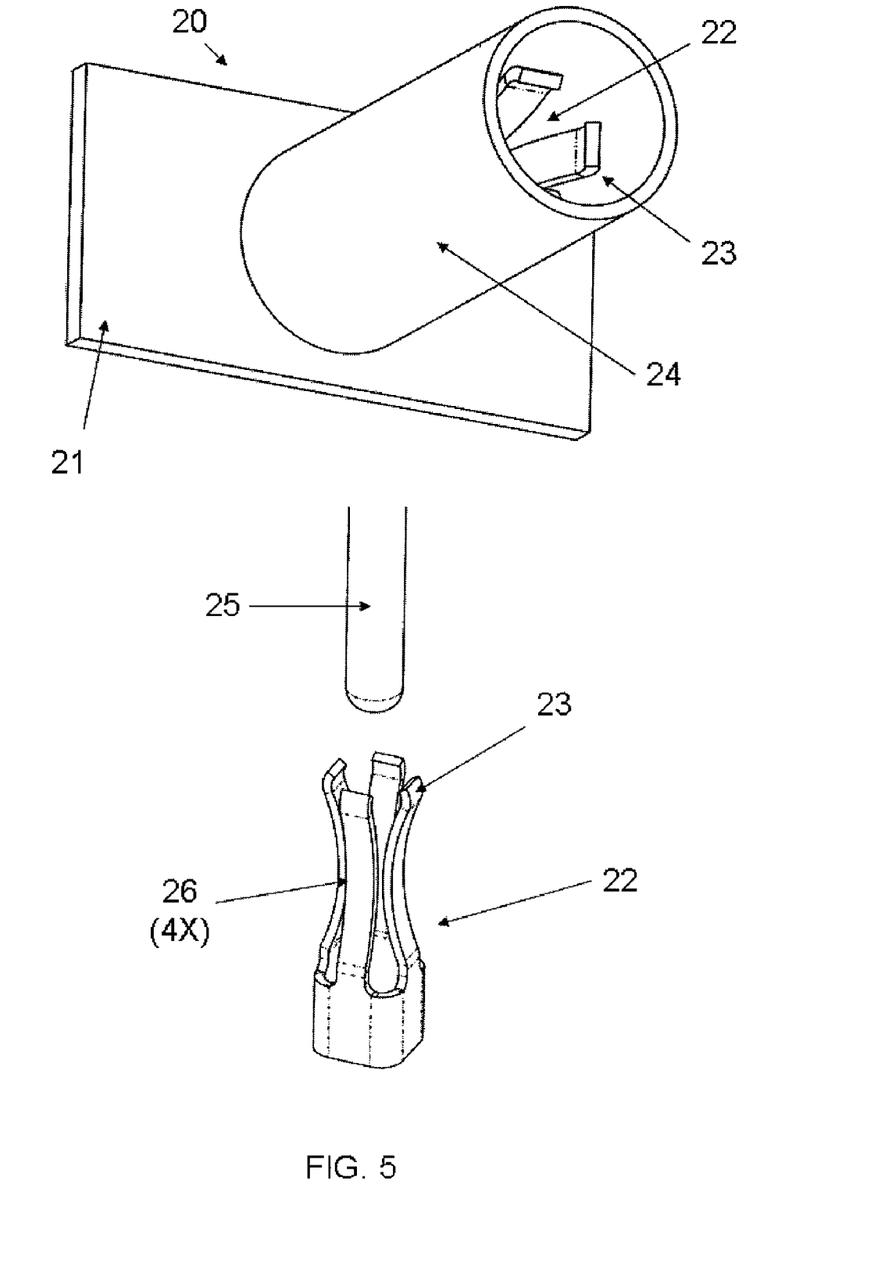
FIG. 5 is an isometric view of an individual female contact forming a portion of the array of the connection receptacles in the lead connector, in accordance with certain embodiments.

FIG. 5 is an isometric view of an individual female contact 20, which is a part of the array of the connection receptacles 10 (FIG. 3b) in the lead connector 4 (FIG. 3b). The contact electrically couples to the lead 2 and is confined within an outer housing 24, which is bonded and held in its array position by a base substrate material 21. Inside the housing 24 is a spring contact 22 fabricated of a noble metal to reduce connection forces. The spring contact 22 has one or more leaf spring surfaces 26, which are urged radially outward by the insertion of a contact pin 25, which is one of an array of feed through pins 7, in the array in the recessed area 6 of the IPG 1. The contact in the specific example has four leaf springs 22. Each leaf 26 is forced outward elastically, and the end surface 23 slides along the inside of the barrel 24 to accommodate the displacement and to provide additional mechanical force and stability.

Figure 6:
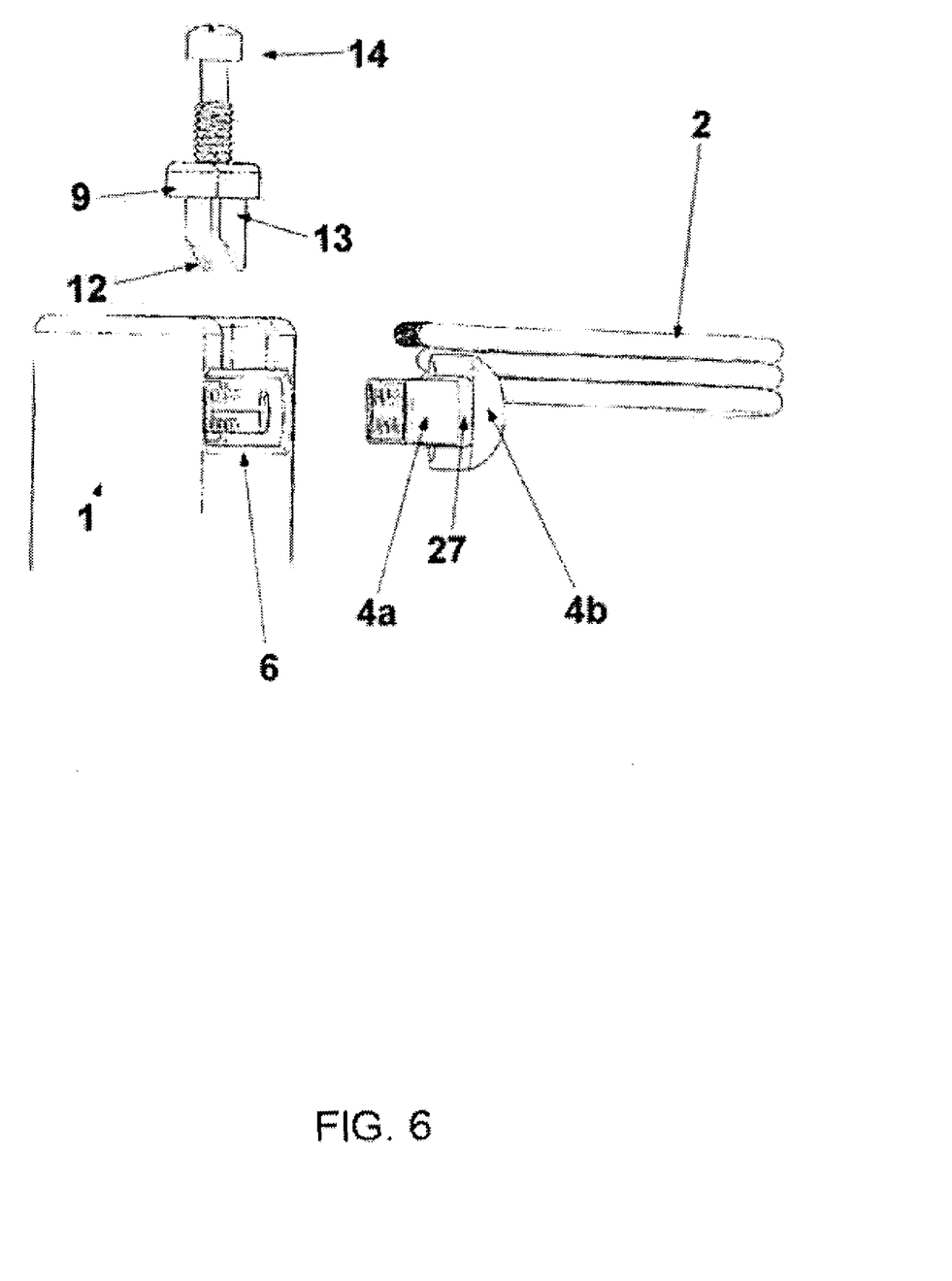
FIG. 6 is an isometric view of a seal on the connector, according to certain embodiments.

FIG. 6 is an isometric view of a sealing ring 27 on the lead connector 4. The lead 2 terminates on the proximal end with a lead connector 4, which exhibits body portion 4a that houses the electrically active contacts and is fully inserted into the recessed area 6 on the IPG 1, a flange portion 4b forms a backbone to the lead connector 4 and extends from the body portion 4a, and where the connector body portion 4a and flange portion 4b meet, a sealing ring 27 is provided. When the lead connector 4 is fully seated into the recessed area 6 on the IPG 1, a seal 27, e.g., a sealing ring, is forced into or presses against the recessed area 6 having inner boundary surfaces that partially compress the seal 27 to prevent intrusion of fluids and/or debris from outside the connection, thereby protecting the electrical connection from fluids. That is, upon establishing the electrical connection, the flange portion 4b is exposed from the exterior of the IPG 1, while the body portion 4a is arranged within the recessed area 6 of the IPG 1, and the seal arranged between body portion 4a and flange portion 4b prevents fluids from entering the recessed area 6.

Figure 7A:
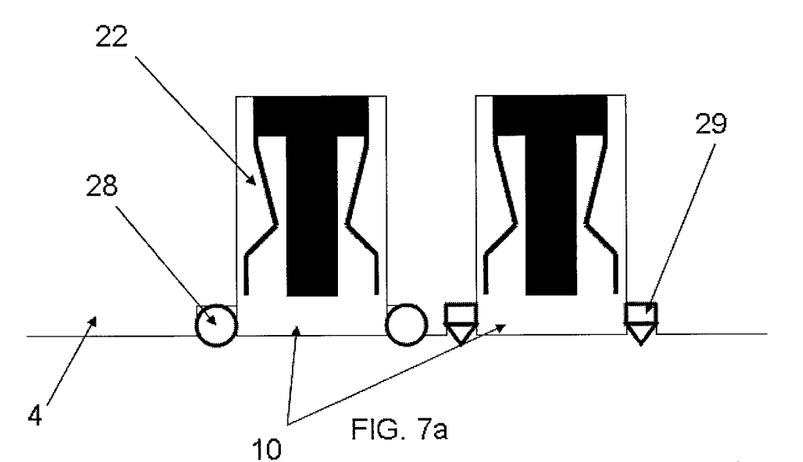
FIG. 7a illustrates another sealing method for the body of the lead connector for contacting contact IPG, in accordance with certain embodiments.

FIG. 7a illustrates an alternative sealing method for the body of the lead connector 4, with the small contact array 10 with metallic female contacts 22 for contacting contact pin 25 of IPG 1. At the surface of the body portion 4a, each barrel 10 is surrounded by a circular seal 28 or 29. The profile of the seal may be circular as in seal 28, forming a torus or ring, or may have an alternative profile, e.g., a projecting v-shape, as with seal 29. The seals 28/29 extend beyond the outer surface of the lead connector 4 so that they are pressed against a facing portion of the recessed area within the recessed area 6 and are deformed upon engagement of the lead connector 4 to the recessed area 6 of the IPG 1. This forms a tight seal and electrical barrier between each connector barrel 10.

While FIG. 7a depicts an implementation in which the recessed area 6 forms a portion of an IPG 1, the sealing method is also applicable to inter-lead or lead-to-adapter or extender embodiments as shown in FIG. 4.

Figure 7B:
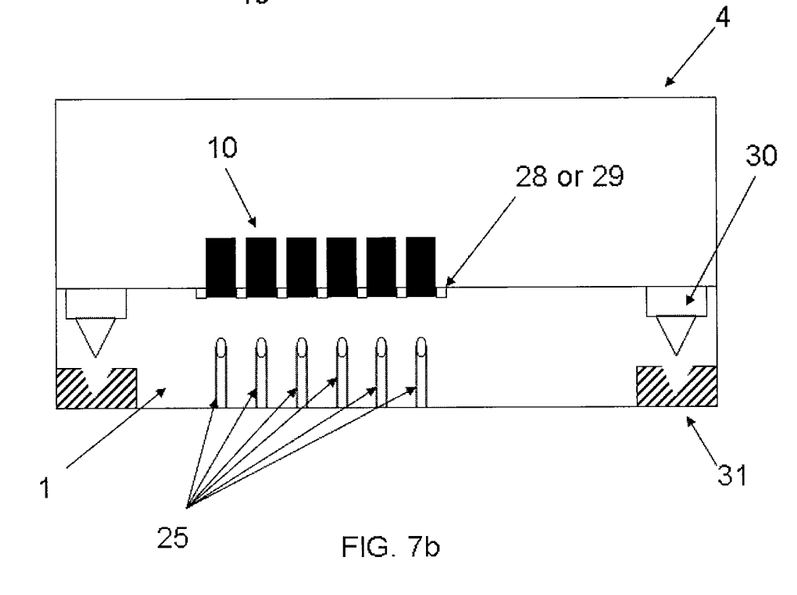
FIG. 7b depicts an alternative view of the body of the lead connector and the IPG of FIG. 7a, and additionally depicts a perimeter seal, in accordance with certain embodiments.

FIG. 7b depicts an alternative view of the body of the lead connector 4 and the IPG 1 of FIG. 7a, showing the same seals 28/29 but also showing a perimeter seal 30 surrounding a periphery of the surface of the body portion 4a, e.g., around the bottom border of the lead connector 4, facing the IPG 1 prior to establishing the electrical connection. This perimeter seal may seal against the bottom surface of the IPG 1 recessed area 6, or may mate with a mirror seal 31 corresponding to the perimeter seal that is bonded to the bottom surface of the recessed area 6. In either embodiment, a water tight seal is formed upon insertion of the lead connector 4 into the IPG recessed area 6. The seals may be further secured by the operation of the connector latch 9, and its securing screw 14.

Figure 8:
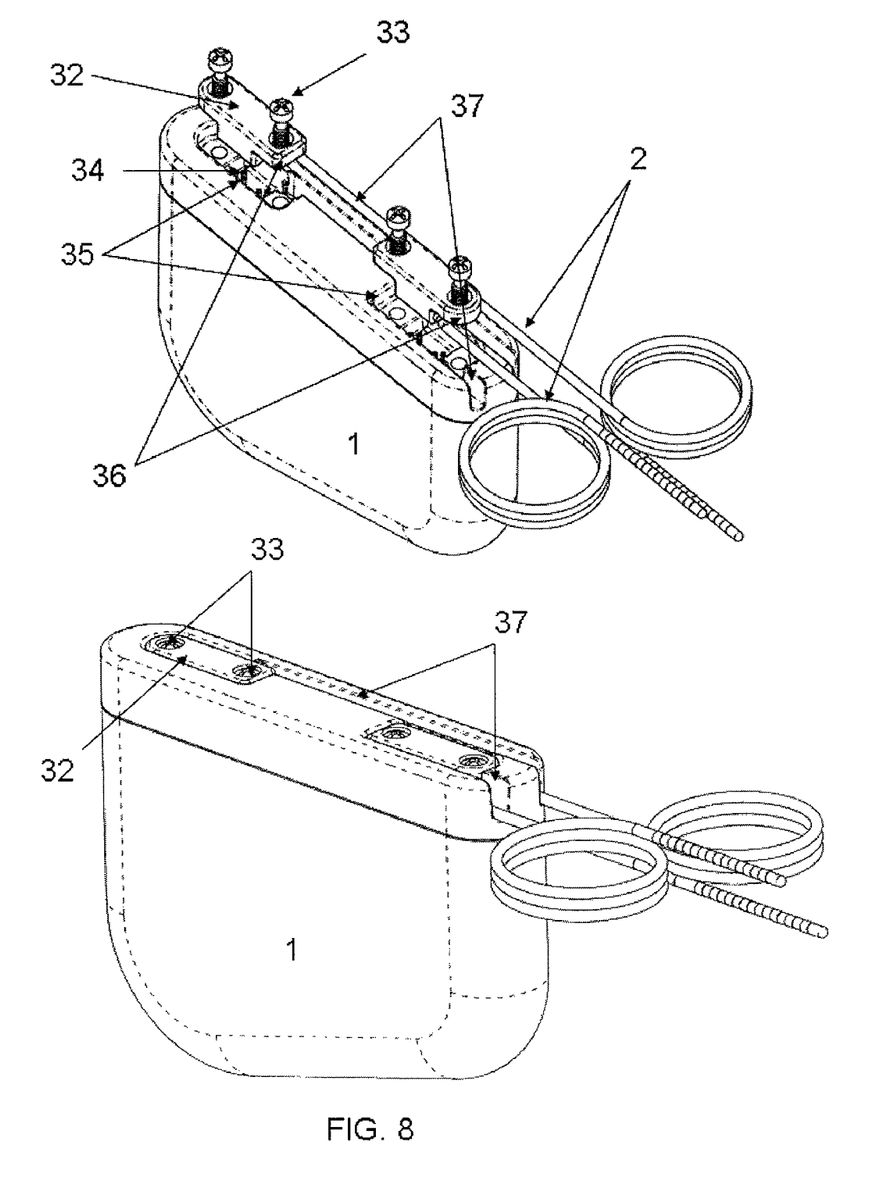
FIG. 8 provides illustrations of another embodiment, in which the lead connections are established on the top of the IPG.

FIG. 8 provides illustrations of an alternative embodiment, where the lead connections are made on top of the IPG 1. The top of the IPG 1 has two recessed areas 35, e.g., receptacles, each presenting with electrically conductive contacts 34, e.g., feed through pins, which are exposed from the IPG 1 prior to establishing the electrical connection. Two patient leads 2 are terminated on their proximal ends with connector blocks 32. The individual connector blocks 32 each include a body portion housing electrically active contacts, a flange portion extending from the body portion, and a lead extending from the connector block 32. However, the connector blocks 32 are oppositely or at least differently shaped, e.g., at a flange portion, to include an orientation and alignment structure 36. Two of many possible configurations for alignment structures 36 are shown in FIG. 8. In the example, the lead 2 exits the connector block 32 from either a square end or a round end 36. These structures 36 guide the movement of the connector blocks 32, so that the barrels (depicted in FIG. 5) register with the electrically conductive contacts 34, and also so that each lead connection is keyed by the structures 36, to ensure the correct lead is connected at each point.

According to FIG. 8, the first and the second recessed areas 35 are defined by sidewalls recessed in the top of IPG 1, and the first recessed area 35 (left) is shaped to accept the first connector block 32, and the second recessed area 35 (right) is shaped to accept the second connector block 32. As a result, the electrical connection may only be established between the first connector block 32 and the first recessed area 35 of the left side of IPG 1 and between second connector block 32 and the second recessed area 34 of the right side of the IPG 1. To secure the connectors 32 to the IPG 1, i.e., to the IPG can, one or more fasteners 33, e.g., two captive screws/securing screws for each connector block 32, are provided and fastener openings are provided in each of the connector block 32 and the IPG recessed areas 35. When the fasteners 33 are inserted into the fastener openings, the connector block 32 is locked to the IPG 1. The connector blocks 32, when engaged, are flush with the surface of the top of the IPG 1. Channels 37 are provided in the upper surface of the IPG 1 and form an opening at a sidewall of the IPG 1. The channels 37 accommodate the body of the patient leads 2 and are shaped to guide the leads 2, allow the lead to extend out of the sidewall of IPG 1, and to provide a gradual flexing region to prevent kinking the lead 2.

To extract the connector block 32 in the example from the body of the IPG 1, the fasteners 33 are backed out. In instances where the fasteners are captive, e.g., using captive screws, prior to the screw threads completely disengaging from the IPG 1, the screws press against the underside of the connector block 32, thus forcing the connector 32 upward and clear of the recessed area 35. Alternately, a prying tool can be used to urge the connector block 32 free of the IPG 1.

From the above description and drawings, it will be understood by those of ordinary skill in the art that the particular embodiments shown and described are for purposes of illustration only and are not intended to limit the scope of the present invention. Those of ordinary skill in the art will recognize that the present invention may be embodied in other specific forms without departing from its spirit or essential characteristics. References to details of particular embodiments are not intended to limit the scope of the invention.

What is claimed is:

1. A connector system for establishing an electrical connection between an implanted medical device and a lead, the connector system comprising:
    an array of electrically active pins and complementary electrically conductive receptacles;
    wherein one of the array and the complementary receptacles are provided in a recessed area of the implanted medical device and are exposed from the implanted medical device prior to establishing the electrical connection, and the other of the array and the complementary receptacles are encased in a lead housing from which a distal end of the lead extends;
    wherein the electrical connection is established upon pressing the pins and the complementary receptacles together;
    wherein upon establishing the electrical connection, the lead housing is exposed at an exterior of the implanted medical device; and
    a latching device for latching the lead housing to the implanted medical device;

wherein the latching device latches the lead housing to the implanted medical device by drawing the lead housing into the recessed area to establish a latched position of the lead housing; and wherein the latching device is reversible, and upon removing the latching device and reinserting the latching device in a reversed position, the latching device presses the lead housing out of its latched position.

2. The connector system according to claim 1, wherein the recessed area of the implanted medical device is provided as a recessed sidewall and the lead housing laterally attaches to the medical device.

3. The connector system according to claim 1, wherein the recessed area of the implanted medical device is provided as a recessed upper wall such that the lead housing attaches to an upper end of the medical device.

4. The connector system according to claim 1, wherein the recessed area and the lead housing further comprise complementary alignment structures for aligning the lead housing with the recessed area prior to establishing the electrical connection.

5. The connector system according to claim 1, wherein the latching device comprises legs that latch the lead housing to the implanted medical device upon being received by latch openings formed in each of the recessed area and the lead housing.

6. The connector system according to claim 5, wherein the legs are chamfered, and as the latching device is inserted into the latch openings, the chamfered legs force the lead housing towards the recessed area to establish a latched position of the lead housing.

7. The connector system according to claim 6, wherein the latching device is reversible so that the legs are received by ejection openings formed in each of the recessed area and the lead housing and force the lead housing out of the latched position.

8. A connector system for establishing an electrical connection between an implanted medical device and a lead, the connector system comprising:

a connector comprising a body portion that houses a plurality of electrically active contacts and a flange portion extending from the body portion, wherein the lead extends from the connector and is coupled to the electrically active contacts;

an implanted medical device comprising a plurality of electrically conductive contacts in a recessed area of the implanted medical device, said electrically conductive contacts exposed from an exterior of the implanted medical device prior to establishing the electrical connection; wherein the electrically active contacts and the electrically conductive contacts establish the electrical connection upon inserting the body portion into the recessed area; and a seal, wherein upon establishing the electrical connection, the seal is arranged between the connector and the implanted medical device and protects the electrical connection from fluids; and a latching device for latching the connector to the implanted medical device, wherein the latching device latches the connector to the implanted medical device by drawing the body portion into the recessed area to establish a latched position of the connector, and wherein the latching device is reversible, and upon removing the latching device and reinserting the latching device in a reversed position, the latching device presses the body portion out from the recessed area and out of the latched position of the connector.

9. The connector system according to claim 8, wherein the seal comprises a sealing ring arranged between the flange portion and the body portion of the connector, and wherein upon insertion of the body portion into the recessed area, the sealing ring presses against the recessed area and seals the electrical connection.

10. The connector system according to claim 8, wherein the seal comprises one or more sealing rings surrounding each of the electrically active contacts, the sealing rings arranged on a surface of the body portion facing the implanted medical device, wherein upon establishing the electrical connection, the sealing rings contact the recessed area and seal the electrical connection.

11. The connector system according to claim 10, wherein the seal further comprises a perimeter seal surrounding a periphery of the surface of the body portion facing the implanted medical device and seals the electrical connection.

12. The connector system according to claim 11, wherein a portion of the recessed area comprises a seal corresponding to the perimeter seal, and wherein the seals mate upon establishing the electrical connection.

13. The connector system according to claim 8, wherein the flange portion is exposed from the exterior of the implanted medical device upon establishing the electrical connection.

* * * * *